United States Patent
Jung et al.

(10) Patent No.: US 11,975,041 B2
(45) Date of Patent: May 7, 2024

(54) COMPOSITION COMPRISING CHP (CYCLO-HIS PRO) FOR PREVENTING, IMPROVING OR TREATING OF BONE LOSS RELATED DISEASE

(71) Applicant: NovMetaPharma Co., Ltd., Seoul (KR)

(72) Inventors: Hoe Yune Jung, Pohang-si (KR); Heon Jong Lee, Incheon (KR); Do Hyun Lee, Pohang-si (KR)

(73) Assignee: NovMetaPharma Co., Ltd., Seoul (KR)

( * ) Notice: Subject to any disclaimer, the term of this patent is extended or adjusted under 35 U.S.C. 154(b) by 127 days.

(21) Appl. No.: 16/764,913

(22) PCT Filed: Nov. 20, 2018

(86) PCT No.: PCT/KR2018/014275
§ 371 (c)(1),
(2) Date: May 18, 2020

(87) PCT Pub. No.: WO2019/098811
PCT Pub. Date: May 23, 2019

(65) Prior Publication Data
US 2020/0338156 A1    Oct. 29, 2020

(30) Foreign Application Priority Data

Nov. 20, 2017    (KR) .......................... 10-2017-0154820

(51) Int. Cl.
| | | |
|---|---|---|
| *A61K 38/00* | (2006.01) | |
| *A61K 35/52* | (2015.01) | |
| *A61K 38/12* | (2006.01) | |
| *A61P 19/10* | (2006.01) | |

(52) U.S. Cl.
CPC .............. *A61K 38/12* (2013.01); *A61K 35/52* (2013.01); *A61P 19/10* (2018.01)

(58) Field of Classification Search
CPC .... A61K 2300/00; A61K 38/12; A61K 33/30; A61K 31/4985; A61K 35/52; A61K 36/48; A61P 19/10; A61P 19/08; A23L 33/10; A23L 33/105; A23V 2002/00; A23V 2200/306
See application file for complete search history.

(56) References Cited

U.S. PATENT DOCUMENTS 5,834,032 A * 11/1998 Song ...................... A61K 31/20
514/6.9
2008/0242621 A1  10/2008 Suh
2009/0004291 A1 * 1/2009 Song ...................... A61K 45/06
424/641

FOREIGN PATENT DOCUMENTS

| CN | 101125201 A | 2/2008 | |
|---|---|---|---|
| CN | 109476701 A | 3/2019 | |
| GB | 2227658 A * | 8/1990 | ........... A61K 38/066 |
| KR | 10-2001-0022786 A | 3/2001 | |
| KR | 10-2006-0105735 A | 10/2006 | |
| KR | 10-2008-0059430 A | 6/2008 | |
| KR | 10-2009-0116836 A | 11/2009 | |
| WO | WO 2000020024 A2 * | 4/2000 | |
| WO | 01/13935 A2 | 3/2001 | |
| WO | 2007/066841 A1 | 6/2007 | |
| WO | 2011093599 A2 | 8/2011 | |
| WO | 2013015611 A2 | 1/2013 | |

OTHER PUBLICATIONS

Tobias John, Paget's Disease and Other Metabolic Bone Disorders, Rheumatology, vol. 53, Issue suppl_1, Apr. 2014 (Year: 2014).*
Yoshikawa et al. Zinc and Lifestyle—Related Disease—with Focus on Diabetes Mellitus and Osteoporosis. Vitam Miner 2013, S6 (Year: 2013).*
Koichi Uyemura et al., "Metabolism and Toxicity of High Doses of Cyclo (his-pro) Plus Zinc in Healthy Human Subjects", Journal of Drug Metabolism & Toxicology—Open Access, Dec. 30, 2010, pp. 1-9, vol. 1• Issue 2•1000105.
Yutaka Yoshikawa et al., "Zinc and Lifestyle—Related Disease—with Focus on Diabetes Mellitus and Osteoporosis", Vitamins & Minerals, 2013, DOI: 10.4172/2376-1318.S6-002, pp. 1-4.
URL:https://stocksmain.tistory.com/84, Jan. 16, 2017, pp. 1-7, Investment, Information on NovMetaPharma.
International Search Report of PCT/KR2018/014275 dated Apr. 16, 2019 [PCT/ISA/210].
Sendak et al., "Newly reported roles of thyroid-stimulating hormone and follicle-stimulating hormone in bone remodelling", International Orthopaedics (SICOT), Apr. 2007, vol. 31, pp. 753-757 (5 pages total).
Rosenthal, M.J. et al., "Effects of arachidonic acid and cyclo (his-pro) on zinc transport across small intestine and muscle tissues", Life Sciences, 2001, pp. 337-348, vol. 70 (12 pages total).
Atik, O.S, et al., "Etiology of Senile Osteoporosis: A Hypothesis", Clinical Orthopaedics and Related Research, 2006, pp. 25-27, No. 443 (3 pages total).
Ming-Yii Huang et al., "Effects of Zinc Compound on Body Weight and Recovery of Bone Marrow in Mice Treated With Total Body Irradiation", Kaohsiung J Med Sci, 2007, pp. 453-462, vol. 23, No. 9 (10 pages total).
International Search Report of PCT/KR2020/006491 dated Sep. 10, 2020 [PCT/ISA/210].

(Continued)

*Primary Examiner* — Aradhana Sasan
*Assistant Examiner* — Mercy H Sabila
(74) *Attorney, Agent, or Firm* — Sughrue Mion, PLLC (57) ABSTRACT

A composition containing cyclo-hispro (CHP) and its use in preventing, alleviating, or treating bone loss diseases are disclosed. The composition contains CHP or a CHP-containing prostate extract.

13 Claims, 4 Drawing Sheets

(56) References Cited

OTHER PUBLICATIONS

Douglas A. Horton, et al., "Exploring privileged structures: the combinatorial synthesis of cyclic peptides", Journal of Computer-Aided Molecular Design, vol. 16, pp. 415-430, 2002, (16 pages).

Alan D. Borthwick, "2,5-Diketopiperazines: Synthesis, Reactions, Medicinal Chemistry, and Bioactive Natural Products", Chemical Reviews, 2012, vol. 112,, pp. 3641-3716, (76 pages).

Adrian Sanchez, et al., "Bioactive peptides: A review", Oxford, Food Quality and Safety, 2017, vol. 1, pp. 29-46, (18 pages).

Hyun Jung Lee, et al., "Preparation of Yeast Hydrolysate Enriched in Cyclo-His-Pro (CHP) by Enzymatic Hydrolysis and Evaluation of its Functionality", Prev. Nutr. Food Sci., 2015, vol. 20, No. 4, pp. 284-291, (8 pages).

Extended European Search Report dated Jun. 21, 2023 in Application No. 20810761.5.

Hongxiu et al., Separation, purification, structural identification and bioactivities of corn cyclo (His-Pro), Food Science, 2016, 37(21): 53-60, with English abstract.

* cited by examiner

COMPOSITION COMPRISING CHP (CYCLO-HIS PRO) FOR PREVENTING, IMPROVING OR TREATING OF BONE LOSS RELATED DISEASE

CROSS REFERENCE TO RELATED APPLICATIONS

This application is a National Stage of International Application No. PCT/KR2018/014275, filed Nov. 20, 2018, claiming priority to Korean Patent Application No. 10-2017-0154820, filed Nov. 20, 2017.

TECHNICAL FIELD

The present invention relates to a composition for preventing, alleviating, or treating bone loss diseases including cyclo-hispro (CHP), and more particularly to a composition for preventing, alleviating, treating bone loss diseases, comprising CHP or a prostate extract including the same.

BACKGROUND ART

Bone modeling and remodeling play an important role in bone development, growth, metabolism. Bone modeling begins in fetal life and continues until young adulthood when the skeleton matures and growth ends, and the maximum bone mass is formed in the 20s and early 30s. Then, for about 30 years, bone remodeling, which involves bone removal and bone supplementation, is repeated, and at this time, bone modeling and bone resorption are paired and balanced. After this period, bone modeling cannot sufficiently compensate for bone loss due to bone resorption, resulting in a decrease in bone mass of about 0.3% to about 0.5% per year, and particularly, women experience a considerable bone loss of 2-3% per year in the early stage of menopause.

Bone tissue constitutes the cartilage and skeletal system, plays a role in mechanical support and muscle attachment, protects living organs and bone marrow, and is responsible for preserving calcium and phosphorus ions to maintain the homeostasis thereof. Bone tissue consists of cell substrates such as collagen and glycoproteins, and various types of cells, including osteoblasts, osteoclasts, and bone cells.

In addition, bone tissue is a dynamic tissue that is formed by osteoblasts and whose destruction and resorption is constantly repeated by osteoclasts. Osteoporosis is a disease caused by an imbalance between osteoblasts and osteoclasts, leading to increased bone resorption compared to bone modeling, and involves thinning of the compact substance of bone due to reduced bone tissue lime, resulting in a widened marrow cavity. As the symptoms progress, a bone becomes weak, and thus is easy to fracture even with a small impact.

Osteoporosis is a condition in which long-term activities are limited not by the symptoms themselves, but by various fractures, especially femur fractures or vertebral fractures, which are easily caused by weakening of bones, and as a result, it is known to provide a cause of 15% of the deaths of the elderly. Bone mass is influenced by many factors, including genetic factors, nutrition, hormonal changes, and differences in exercise and lifestyle, and the causes of osteoporosis are old age, lack of exercise, low weight, smoking, low calcium diet, menopause, ovarian ablation, and the like. In particular, in women, bone loss continues to progress after the age of 30, and bone loss rapidly progresses due to hormonal changes in menopause.

As such, osteoporosis differs in terms of severity, but is an unavoidable symptom in the elderly, especially in postmenopausal women. In developed countries, as the population ages, interest in osteoporosis and therapeutic agents thereof is gradually increasing. In addition, it is known that, around the world, there is a market of about 130 billion dollars related to the treatment of bone diseases, and it is expected to increase further in the future. Thus, global research institutes and pharmaceutical firms are investing heavily in the development of therapeutic agents for bone diseases, and the development of bone resorption inhibitors is actively ongoing.

Recently, it has been reported that the effect of a calcium-reinforcing agent, which is widely used as a therapeutic agent for osteoporosis, is insignificant, and it is also reported that the therapeutic effect of hormone therapy using estrogen or calcitonin is insignificant. In particular, it is reported that hormone therapy including estrogen or calcitonin increases bone mineral density and lowers the onset of rectal cancer, but side effects such as breast cancer, myocardial infarction, and venous thrombosis have been reported. In addition, bisphosphonates, which are widely used as a therapeutic agent for osteoporosis, are attracting attention as a new alternative therapeutic agent, but when improperly administered orally, lesions may be observed in the upper airway. Therefore, since osteoporosis is a disease that cannot be cured only by short-term administration of a drug and essentially requires long-term administration of a drug, there is an urgent need to develop a novel material that has a new action and skeletal structure and reduced toxicity and side effects, and thus is effective in preventing and treating osteoporosis.

Meanwhile, prior to the present invention, an anti-diabetic composition including zinc ions and cyclo-hispro (CHP) has been disclosed, but there is no report of the effect of CHP on preventing, alleviating, or treating bone loss diseases.

DESCRIPTION OF EMBODIMENTS

Technical Problem

An object of the present invention is to provide a pharmaceutical composition for the prevention or treatment of bone loss diseases, including cyclo-hispro.

Another object of the present invention is to provide a health functional food composition for the prevention or alleviation of bone loss diseases, including cyclo-hispro.

Another object of the present invention is to provide a pharmaceutical composition for the prevention or treatment of bone loss diseases, including a prostate extract.

Another object of the present invention is to provide a health functional food composition for the prevention or alleviation of bone loss diseases, including a prostate extract.

Technical Solution

According to an aspect of the present disclosure, there is provided a pharmaceutical composition for the prevention or treatment of a bone loss disease, including cyclo-hispro or a pharmaceutically acceptable salt thereof.

The present invention also provides a health functional food composition for the prevention or alleviation of a bone loss disease, including cyclo-hispro.

The present invention also provides a pharmaceutical composition for the prevention or treatment of a bone loss disease, including a prostate extract.

The present invention also provides a health functional food composition for the prevention or alleviation of a bone loss disease, including a prostate extract.

According to another exemplary embodiment of the present invention, the bone loss disease may be any one or more selected from osteoporosis, Paget's disease, alveolar bone loss, osteomalacia, and renal osteodystrophy.

According to another exemplary embodiment of the present invention, the osteoporosis may be caused by a decrease in female hormones.

Advantageous Effects of Invention

A composition for preventing, alleviating, or treating bone loss diseases including cyclo-hispro or a prostate extract, according to the present invention, has an excellent effect of promoting osteogenic differentiation and enhancing bone mineral density, and thus is effective in treating bone loss diseases.

BEST MODE

Hereinafter, the present invention will be described in more detail.

As described above, the inventors of the present invention discovered that, through the effect of alleviating osteoporosis and promoting osteogenic differentiation in an ovariectomized animal model, cyclo-hispro is effective in preventing, alleviating, or treating bone loss diseases, and thus completed the present invention.

Therefore, the present invention provides a pharmaceutical composition for the prevention or treatment of a bone loss disease, including cyclo-hispro or a prostate extract.

The present invention also provides a health functional food composition for the prevention or alleviation of a bone loss disease, including cyclo-hispro or a prostate extract.

As used herein, "cyclo-hispro (CHP)" refers to a naturally occurring cyclic dipeptide consisting of histidine and proline, which are metabolites of thyrotropin-releasing hormone (TRH), or a bioactive dipeptide that is also synthesized de novo in the body through TRH metabolic processes, and refers to a substance widely distributed throughout the brain and in the spinal cord, gastrointestinal tract, and the like.

In the composition of the present invention, the CHP may be synthesized CHP or commercially available CHP. In addition, the CHP may be CHP purified from a CHP-containing material, e.g., a prostate extract.

The term "purified" is used to mean that CHP is in a concentrated form compared to a form that can be obtained from natural sources such as a prostate extract. Purified ingredients may be obtained from natural sources thereof by concentration or chemical synthesis.

The main components of the "prostate extract" are zinc, CHP, a prostaglandin precursor, and arachidonic acid, and since a high concentration of CHP is included therein, it can be reasonably expected that CHP induces the effect of increasing bone mineral density and a bone volume fraction and promoting osteogenic differentiation and bone modeling.

In the composition of the present invention, the "prostate extract" may be prostate powder of a cow or pig, or the like, and preferably, may be in a form in which fat is removed to increase the content of CHP, but the present invention is not limited thereto.

As used herein, the term "bone loss" refers to a symptom of bone loss caused by an imbalance between osteoclasts and osteoblasts, and the term "bone loss disease" means to encompass all diseases associated with the above symptoms. Thus, the bone loss disease encompasses all diseases that are caused by reduced bone mineral density resulting from bone loss due to excessively increased activity of osteoclasts, or that result from the non-occurrence of smooth bone modeling due to reduced activity of osteoblasts. Specific examples of the bone loss disease include, but are not limited to, osteoporosis, Paget's disease, alveolar bone loss, osteomalacia, and renal osteodystrophy.

In this regard, the osteoporosis may occur due to a decrease in female hormones as one of the symptoms of the climacterium or menopause, or due to the destruction of osteoblasts or the inhibition of activity thereof.

As used herein, the term "climacterium" refers to a transition from the period with reproductive function to the period with complete loss of reproductive function. The climacterium is mainly used to refer to the climacterium of women, but the climacterium of women includes not only menopause but also the period before and after perimenopause, and generally corresponds to an age group of 40-60 years.

The composition including CHP or a prostate extract of the present invention may promote bone modeling by promoting osteogenic differentiation, thus being able to prevent, alleviate, or treating bone loss diseases.

In the composition for the prevention, alleviation, or treatment of a bone loss disease according to the present invention, the term "prevention" means all actions that inhibit or delay the onset of a disease or a symptom. In the present invention, the term "prevention" means, by promoting osteogenic differentiation, delaying the onset of a bone loss disease or inhibiting the onset of the disease.

In the composition for the prevention, alleviation, or treatment of a bone loss disease according to the present invention, the term "alleviation" refers to all actions that improve or beneficially change a disease or a condition of the disease, and in the present invention, means, through the promotion of osteogenic differentiation, improving symptoms of osteoporosis or symptoms such as alveolar bone loss.

In the composition for the prevention, alleviation, or treatment of a bone loss disease according to the present invention, the term "treatment" refers to all actions that delay, stop, or reverse a disease or condition, and in the present invention, means, through the promotion of osteogenic differentiation, stopping, relieving, alleviating, eliminating, or reversing alveolar bone loss or bone loss.

Figure 1:
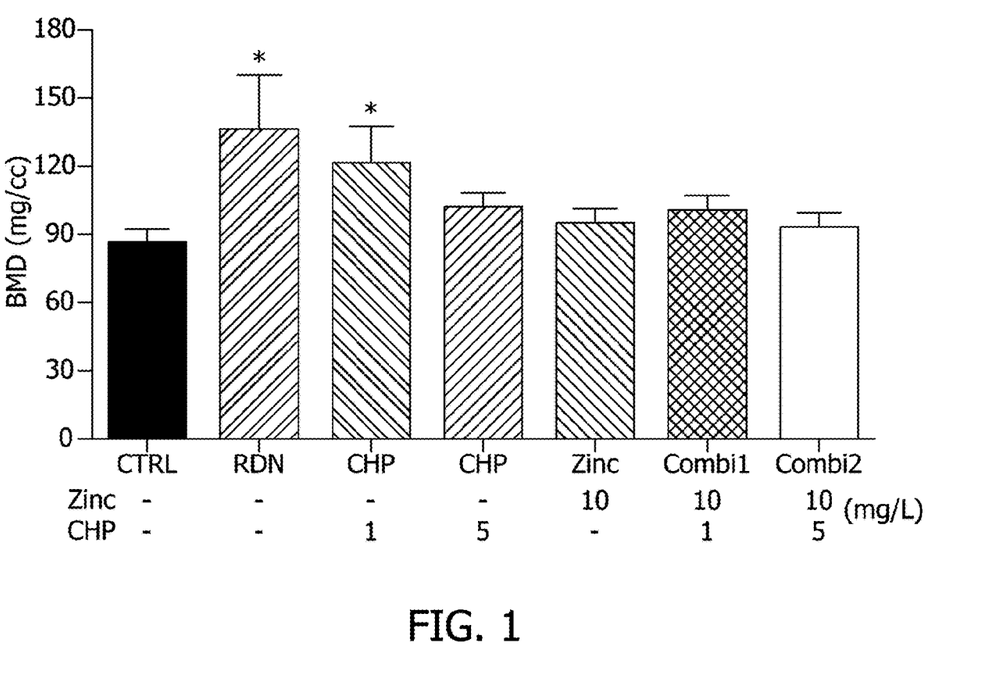
FIG. 1 is a graph showing the results of analyzing changes in bone mineral density of a femur by cyclo-hispro (CHP) administration.
Figure 2:
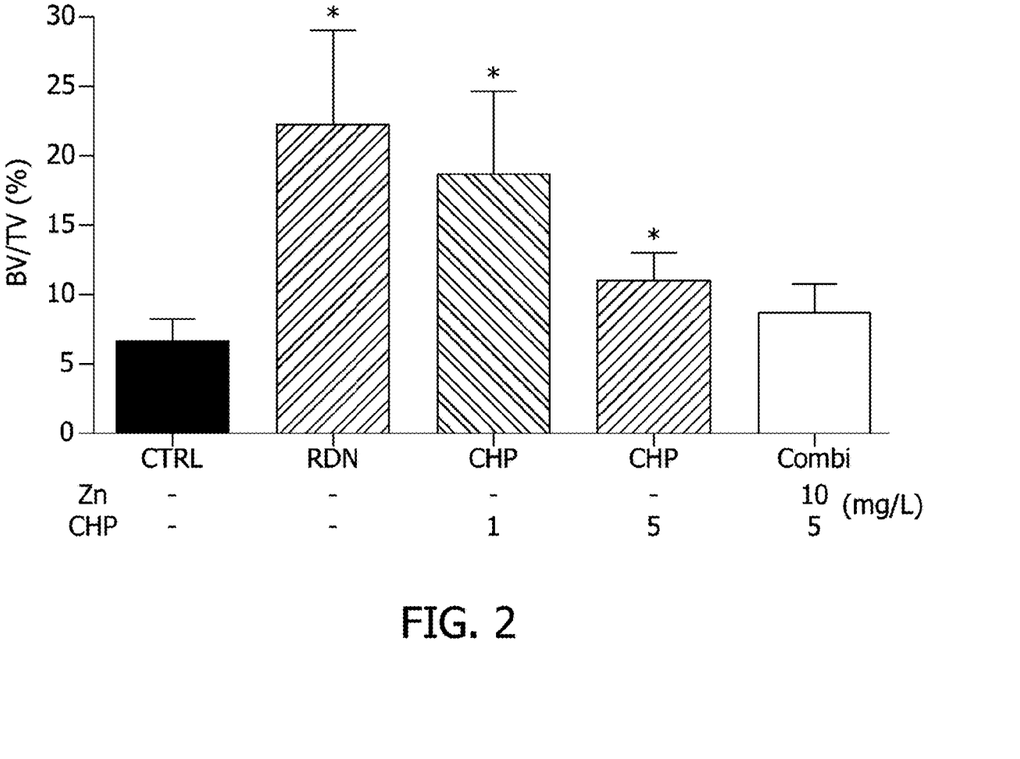
FIG. 2 is a graph showing the results of analyzing changes in bone volume fraction by cyclo-hispro (CHP) administration.

In one embodiment of the present invention, as a result of administering CHP alone to an ovariectomized animal model, as illustrated in FIGS. 1 and 2, it was confirmed that the bone mineral density and bone volume fraction of a femur were significantly increased. This effect of CHP was significantly stronger than those of a zinc salt-administered group and a combined administration group administered a mixture of a zinc salt and CHP, through which it can be inferred that the CHP-induced increase in bone mineral density was not due to a previously known effect of increasing in vivo zinc absorption.

Figure 3:
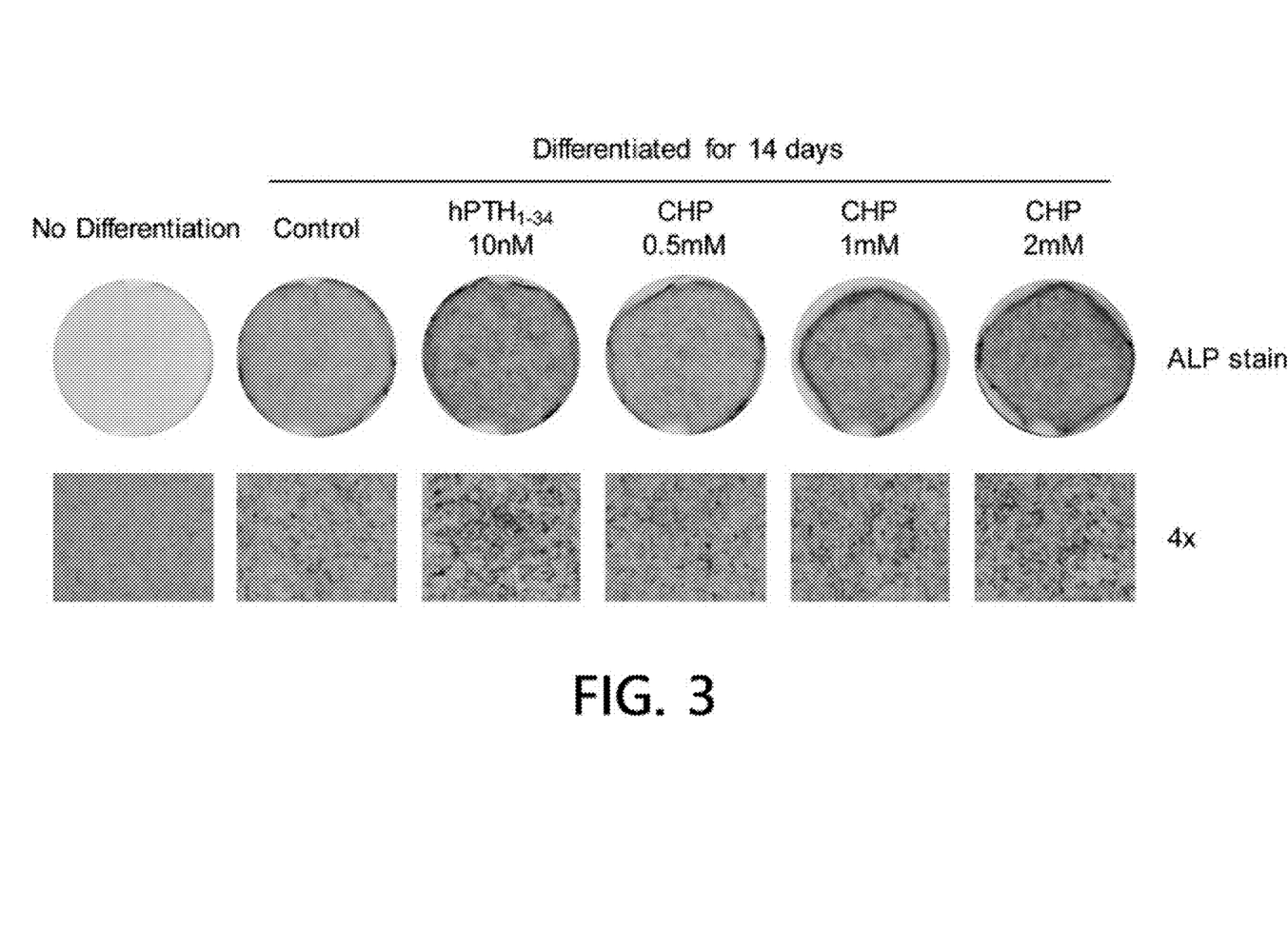
FIG. 3 illustrates the results of confirming the effect of promoting osteogenic differentiation by cyclo-hispro (CHP) administration.
Figure 4:
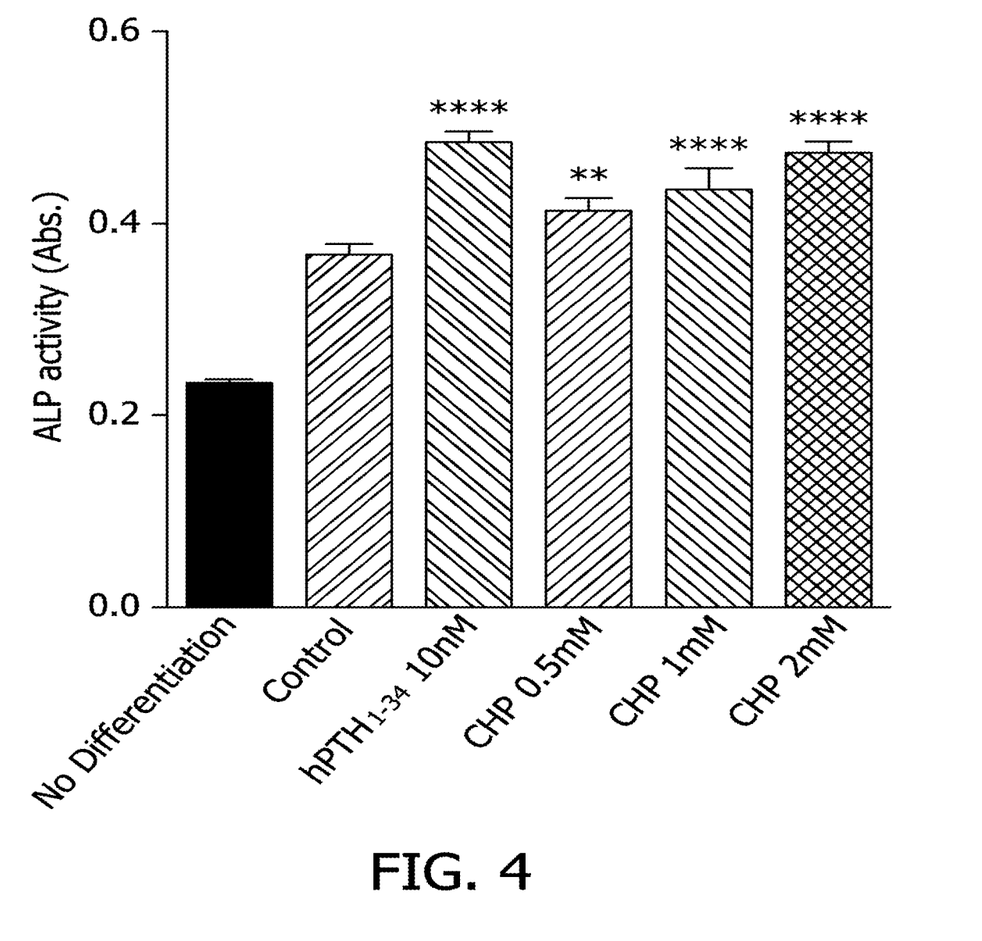
FIG. 4 is a graph showing the effect of increasing ALP activity by cyclo-hispro (CHP) administration.

In another embodiment of the present invention, the osteogenic differentiation effect by CHP treatment was confirmed. As a result, as illustrated in FIG. 3, it was confirmed that, as the concentration of CHP treated was increased, osteogenic differentiation and bone modeling were promoted, and an increase in the promotion was greater than that in a negative control. In particular, as illustrated in FIG. 4, it was confirmed that CHP promoted osteogenic differentiation and bone modeling by increasing the activity of ALP, and an ALP-promoting activity that is the same or similar to that of a positive control (hPTH$_{1-34}$ 10 nM) was observed in a group treated with 2 mM CHP. In the composition for the prevention, alleviation, or treatment of a bone loss disease according to the present invention, CHP may be administered at 0.1 mg/L to 5 mg/L, preferably 0.5 mg/L to 3 mg/L.

As used herein, the term "pharmaceutically acceptable" refers to physiologically acceptable and that which generally does not cause allergic responses or responses similar thereto, when administered to a human, and the salt may be an acid addition salt formed by a pharmaceutically acceptable free acid.

The pharmaceutically acceptable salt may be an acid addition salt formed using an organic acid or an inorganic acid, and the organic acid includes, for example, formic acid, acetic acid, propionic acid, lactic acid, butyric acid, isobutyric acid, trifluoroacetic acid, malic acid, maleic acid, malonic acid, fumaric acid, succinic acid, monoamide succinate, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxy acetic acid, benzenesulfonic acid, p-toluenesulfonic acid, or methanesulfonic acid. The inorganic acid includes, for example, hydrochloric acid, bromic acid, sulfuric acid, phosphoric acid, nitric acid, carbonic acid, or boric acid. The acid addition salt may preferably be in the form of a hydrochloride or acetate, and more preferably in the form of a hydrochloride.

In addition, possible salt forms include GABA salts, gabapentin salts, pregabalin salts, nicotinates, adipates, hemimalonates, cysteine salts, acetylcysteine salts, methionine salts, arginine salts, lysine salts, ornithine salts, aspartates, or the like.

In addition, the pharmaceutical composition of the present invention may further include a pharmaceutically acceptable carrier. Pharmaceutically acceptable carriers may further include, for example, carriers for oral administration or carriers for parenteral administration. Carriers for oral administration may include lactose, starch, cellulose derivatives, magnesium stearate, stearic acid, and the like. Carriers for parenteral administration may include water, suitable oils, saline, aqueous glucose, glycols, and the like. In addition, stabilizers and preservatives may be further included. Suitable stabilizers include antioxidants such as sodium hydrogen sulfite, sodium sulfite, or ascorbic acid. Suitable preservatives include benzalkonium chloride, methyl- or propyl-parabens, and chlorobutanol. For other pharmaceutically acceptable carriers, reference can be made to those described in the following literature (Remington's Pharmaceutical Sciences, 19th ed., Mack Publishing Company, Easton, PA, 1995).

The pharmaceutical composition of the present invention may be administered by any method to mammals, including humans. For example, the pharmaceutical composition may be administered orally or parenterally, and the parenteral administration method may be, but is not limited thereto, intravenous administration, intramuscular administration, intraarterial administration, intramedullary administration, intradural administration, intracardiac administration, transdermal administration, subcutaneous administration, intraperitoneal administration, intranasal administration, enteral administration, local administration, sublingual administration, or intrarectal administration.

The pharmaceutical composition of the present invention may be formulated into a preparation for oral administration or parenteral administration depending on the route of administration as described above. When the pharmaceutical composition is formulated, one or more buffers (e.g., saline or PBS), carbohydrates (e.g., glucose, mannose, sucrose, or dextran), antioxidants, bacteriostatic agents, chelating agents (e.g., EDTA or glutathione), fillers, extenders, binders, adjuvants (e.g., aluminum hydroxide), suspending agents, thickeners, wetting agents, disintegrants or surfactants, and diluents or excipients may be used.

Solid preparations for oral administration include tablets, pills, powders, granules, liquids, gels, syrups, slurries, suspensions, capsules, and the like. Such solid preparations may be prepared by mixing the pharmaceutical composition of the present invention with at least one excipient such as starch (including corn starch, wheat starch, rice starch, potato starch, and the like), calcium carbonate, sucrose, lactose, dextrose, sorbitol, mannitol, xylitol, erythritol, maltitol, cellulose, methyl cellulose, sodium carboxymethyl cellulose, hydroxypropyl methylcellulose, or gelatin. For example, tablets or sugar-coated tablets may be obtained by blending an active ingredient with a solid excipient, grinding the blend, adding a suitable adjuvant thereto, and then processing the resultant into a granular mixture.

In addition to simple excipients, lubricants such as magnesium stearate talc are also used. Liquid preparations for oral use include suspensions, liquids for internal use, emulsions, syrups, and the like, and in addition to water or liquid paraffin, which is a commonly used simple diluent, the liquid preparations may include various excipients, e.g., a wetting agent, a sweetener, a fragrance, and a preservative.

In addition, in some cases, crosslinked polyvinylpyrrolidone, agar, alginic acid, sodium alginate, or the like may be added as a disintegrant, and an anti-coagulant, a lubricant, a wetting agent, a flavoring agent, an emulsifying agent, a preservative, and the like may be further included.

For parenteral administration, the pharmaceutical composition of the present invention may be formulated according to a method known in the art into the form of an injection, a transdermal delivery agent, and a nasal inhalant along with suitable parenteral carriers. Such injections must be sterile and protected from contamination of microorganisms such as bacteria and fungi. Examples of suitable carriers for injections include, but are not limited to, solvents or dispersion media, including water, ethanol, polyols (e.g., glycerol, propylene glycol, and liquid polyethylene glycol), mixtures thereof, and/or vegetable oils. More preferably, suitable carriers include isotonic solutions such as Hanks' solution, Ringer's solution, phosphate buffered saline (PBS) containing triethanolamine or sterile water for injection, 10% ethanol, 40% propylene glycol, and 5% dextrose, and the like. To protect the injections from microbial contamination, various antibacterial and antifungal agents such as parabens, chlorobutanol, phenol, sorbic acid, thimerosal, and the like may be further included. In addition, most of the injections may further include an isotonic agent such as sugar or sodium chloride.

Examples of the transdermal delivery agent include ointments, creams, lotions, gels, liquid for external application, pastes, liniments, aerosols, and the like. The term "transdermal delivery" as used herein means that the pharmaceutical composition is topically administered to the skin such that an effective amount of the active ingredient included in the pharmaceutical composition is delivered to the skin.

For the inhalants, the compound used according to the present invention may be conveniently delivered in the form of aerosol spray from a pressurized pack or a nebulizer using a suitable propellant, for example, dichlorofluoromethane, trichlorofluoromethane, dichlorotetrafluoroethane, carbon dioxide, or other suitable gases. In the case of pressurized aerosols, a dosage unit may be determined by providing a valve configured to deliver a metered amount. For example, gelatin capsules and cartridges for use in inhalers or blowers may be formulated to include a powder mixture of a compound and a suitable powder base such as lactose or starch. Formulations for parenteral administration are described in the reference, which is a prescription commonly known for all pharmaceutical chemistry (Remington's Pharmaceutical Science, 15th Edition, 1975. Mack Publishing Company, Easton, Pennsylvania 18042, Chapter 87: Blaug, Seymour).

The pharmaceutical composition of the present invention may provide a desirable effect of preventing, alleviating, or treating a bone loss disease when including an effective amount of cyclo-hispro or a prostate extract. As used herein, the term "effective amount" refers to an amount that is more responsive than a negative control, and preferably refers to an amount sufficient to prevent, alleviate, or treat bone loss diseases. The pharmaceutical composition of the present invention may include 0.01% to 99.9% of cyclo-hispro or a prostate extract, and may include the remainder as a pharmaceutically acceptable carrier. The effective amount of the cyclo-hispro or prostate extract included in the pharmaceutical composition of the present invention may vary depending on the form in which the composition is commercialized, or the like.

A total effective amount of the pharmaceutical composition of the present invention may be administered to a patient in a single dose, and may be administered by a fractionated treatment protocol which is administered in multiple doses for a long period of time. In the pharmaceutical composition of the present invention, the amount of the active ingredient may vary depending on the severity of disease. For example, a daily dosage of cyclo-hispro may be administered in an amount of preferably, 0.001 mg to 100 mg, more preferably 0.01 mg to 10 mg, per body weight (1 kg) in a single dose or multiple doses. However, an effective dosage level of the cyclo-hispro or prostate extract may be determined in consideration of various factors including not only the administration route of the pharmaceutical composition and the number of treatments, but also the age, body weight, health conditions of patients, gender, the severity of disease, diet, excretion rate, and the like. Thus, considering these factors, a suitable effective dosage level of the cyclo-hispro or prostate extract may be determined by those of ordinary skill in the art depending on specific applications for preventing, treating, or alleviating bone loss diseases. The pharmaceutical composition according to the present invention is not particularly limited in terms of formulation, administration route, and administration method as long as it exhibits the effects of the present invention.

The pharmaceutical composition for the prevention or treatment of a bone loss disease according to the present invention may be used alone or in combination with surgery, radiation therapy, hormone therapy, chemotherapy, or methods using a biological response modifier.

The pharmaceutical composition for the prevention or treatment of a bone loss disease according to the present invention may also be provided in the form of a formulation for external use, including cyclo-hispro or a prostate extract. In this regard, the composition of the present invention may be a quasi-drug composition for the prevention or alleviation of a bone loss disease and a quasi-drug including the composition.

The formulation for external use may be applied directly to the skin or the oral cavity. When used as a preparation for external application, the pharmaceutical composition for the prevention or treatment of a bone loss disease according to the present invention may further include adjuvants commonly used in dermatology, such as other ingredients commonly used in preparations for external application to the skin, for example, fatty substances, organic solvents, solubilizing agents, thickeners and gelling agents, softeners, antioxidants, suspending agents, stabilizers, foaming agents, fragrances, surfactants, water, ionic or non-ionic emulsifiers, fillers, metal ion blocking agents, chelating agents, preservatives, vitamins, blocking agents, wetting agents, essential oils, dyes, pigments, hydrophilic or lipophilic active agents, lipid vesicles, or the like. In addition, the above-listed ingredients may be introduced in an amount generally used in the dermatology field.

When the composition of the present invention is provided as a dermatologic agent, the preparation may be in the form of, but is not limited to, a formulation such as liquid, an ointment, a patch, a gel, a cream, an aerosol, or the like. According to one embodiment of the present invention, the quasi-drug may include oral care products including toothpastes, mouthwashes, and mouth sprays, ointments, masks, wetting agents, plasters, percutaneous absorbents, and the like.

When treated with the cyclo-hispro of the present invention, osteogenic differentiation was promoted. Thus, when the active ingredient is applied to oral care products, it is effective in preventing or alleviating alveolar bone disease by promoting osteogenic differentiation. Therefore, the quasi-drug composition may be a composition for oral care for the prevention or alleviation of bone loss.

When the composition of the present invention is used as a quasi-drug composition, cyclo-hispro or a prostate extract may be added as it is or may be suitably used according to a general method along with other quasi-drug ingredients. The amounts of active ingredients to be mixed may be appropriately determined according to the purpose of use (for prevention, health, or therapeutic treatment).

For the quasi-drug composition and quasi-drug of the present invention, the above descriptions of the pharmaceutical composition and health functional food composition of the present invention can be applied mutatis mutandis.

As used herein, the term "health functional food" encompasses all meanings of "functional foods" and "health foods."

As used herein, the term "functional food" is the same as the term "food for special health use (FoSHU)" and refers to foods with potent pharmaceutical and medical effects which are processed so that bio-regulatory functions can be efficiently exhibited.

As used herein, the term "health food" means foods having an active health maintenance or enhancement effect compared to general foods, and health supplement foods mean foods for the purpose of health supplement. In some cases, the terms functional food, health food, and health supplement are used interchangeably. To obtain a useful effect of the food on alleviating or recovering bone loss diseases, the food may be prepared in various forms such as tablets, capsules, powders, granules, liquids, and pills.

Specific examples of these functional foods include processed foods that are modified so as to utilize the characteristics of agricultural products, livestock products, or fishery products using the above composition and that also have good storage properties.

The health functional food composition of the present invention may also be prepared in the form of nutritional supplements, food additives, feed, and the like, and fed to animals including humans or livestock.

The types of food compositions may be prepared in various forms according to a general method known in the art. The food compositions may be prepared by adding cyclo-hispro or a prostate extract to general foods including, but not being limited to, beverages (including alcoholic beverages), fruits and processed foods thereof (e.g., canned fruits, bottled foods, jam, marmalade, and the like), fish, meat and processed foods thereof (e.g., ham, sausage, corn, beef, and the like), bread and noodles (e.g., Japanese-style noodles, buckwheat noodles, ramen, spaghetti, macaroni, and the like), fruit juices, various drinks, cookies, taffy, dairy products (e.g., butter, cheese, and the like), edible vegetable oils, margarine, vegetable proteins, retort foods, frozen foods, various seasonings (e.g., soybean paste, soy sauce, other sauces, and the like), and the like.

In addition, the nutritional supplements may be prepared by adding cyclo-hispro or a prostate extract into the form of capsules, tablets, pills, or the like, but the present invention is not limited thereto.

In addition, as a health functional food, for example, cyclo-hispro or a prostate extract may be prepared into the form of tea, juice, and drink, and then may be liquefied, granulated, encapsulated, and powdered so that the food can be ingested as a health drink, but the present invention is not limited thereto. In addition, to be used in the form of a food additive, the cyclo-hispro or prostate extract may be prepared into a powder or concentrate form. In addition, the cyclo-hispro or prostate extract may be mixed with known active ingredients known to be effective in preventing or alleviating bone loss diseases and prepared into the form of a composition.

When the food composition of the present invention is a health beverage composition, the health beverage composition may include various flavor enhancers, natural carbohydrates, or the like as additional ingredients like general beverages. The above-described natural carbohydrates include monosaccharides such as glucose and fructose; disaccharides such as maltose and sucrose; polysaccharides such as dextrin and cyclodextrin; and sugar alcohols such as xylitol, sorbitol, and erythritol. As sweeteners, natural sweeteners such as thaumatin and stevia extracts, and synthetic sweeteners such as saccharin and aspartame may be used. The proportion of the natural carbohydrates generally ranges from about 0.01 g to about 0.04 g, preferably about 0.02 g to 0.03 g, per 100 mL of the composition of the present invention.

The cyclo-hispro or prostate extract may be included as an active ingredient of the food composition for the prevention or alleviation of a bone loss disease, and the amount thereof is an effective amount sufficient to obtain the prevention or alleviation effect and preferably ranges from, for example, 0.01 wt % to 100 wt % with respect to a total weight of the composition, but is not particularly limited. The food composition of the present invention may be prepared by mixing the cyclo-hispro or prostate extract with other active ingredients known to be effective in preventing or alleviating bone loss diseases.

In addition to the above-listed ingredients, the health functional food of the present invention may include various nutrients, vitamins, electrolytes, a flavoring agent, a colorant, pectic acid and a salt thereof, alginic acid and a salt thereof, organic acids, a protective colloidal thickening agent, a pH adjusting agent, a stabilizer, a preservative, glycerin, alcohols, carbonating agents, or the like. In addition, the health food of the present invention may include pulp for preparing natural fruit juices, fruit beverages, or vegetable beverages. These ingredients may be used alone or a mixture thereof may be used. The proportion of these additives is not very important, but the amounts of the additives generally range from 0.01 part by weight to 0.1 part by weight with respect to 100 parts by weight of the composition of the present invention.

Hereinafter, the present invention will be described in further detail with reference to the following examples. As the present invention allows for various changes and numerous forms, the particular embodiments set forth herein and descriptions are provided only to facilitate the understanding of the present invention, and are not intended to limit the present invention to particular forms of disclosure. The scope of the present invention should be understood as encompassing all changes, equivalents, and substitutes that fall within the technical spirit and scope of the present invention.

MODE OF INVENTION

Preparation Example

The zinc salt used in the following examples was purchased from Captek Softgel International, and cyclo-hispro (CHP) was purchased from Bachem and used. Parathyroid hormone$_{1-34}$ (hPTH$_{1-34}$) as a positive control was purchased from Torqueless. In culturing osteoblasts, MEMα available from Gibco was used, and ascorbic acid-free media and FBS available from Hyclone were used, and β-glycerophosphate and ascorbic acid, which were used for differentiation, were purchased from Sigma Aldrich. To measure the activity of alkaline phosphatase (ALP), a 1-STEP™ NBCT/BCIP solution available from Thermo was used.

Example 1

Evaluation of Osteoporosis Alleviation Effect Using Ovariectomized Animal Model by Administration of CHP, Zinc Salt, or Mixture Thereof 1-1. Design of Experimental Animals and Experimental Material Treatment Composition To determine the effect of alleviating osteoporosis in an ovariectomized animal model according to administration of CHP, a zinc salt, or a mixture thereof, 20-week-old SD female mice (SLC/Central Experimental Animal Co. Ltd., Seoul, Korea) were purchased and raised under certain conditions (temperature: 22±2° C., relative humidity: 55±10%, light/dark cycle: 12 hours). 7 mice/group were allowed to freely drink water and eat food in a cage, subjected to an adaptation period of 1 week before the experiment, and used in the experiment. After the adaptation period, the mice were divided into 7 groups and as shown in Table 1, administration of CHP, a zinc salt, or a mixture thereof was performed in drinking water, and in the case of the positive control, risedronate was subcutaneously administered once a week.

TABLE 1

| Group | CHP (mg/L) | Zinc salt (mg/L) | Risedronate (mg/kg) |
|---|---|---|---|
| Ovariectomized control | — | — | — |
| CHP-administered group 1 | 1 | — | — |
| CHP-administered group 2 | 5 | — | — |
| Zinc salt-administered group | — | 10 | — |
| Mixture-administered group 1 | 1 | 10 | — |
| Mixture-administered group 2 | 5 | 10 | — |
| Positive Control (Risedronate) | — | — | 10 |

1-2. Micro CT Measurement

After 6 weeks of the administration of CHP, a zinc salt, or a mixture thereof, the effect of alleviating osteoporosis in an ovariectomized animal model was analyzed using Micro CT. The bone mineral density of ovariectomized animals was measured by bone CT scanning of the 3 mm range at the front side of a 2 mm femoral growth plate using micro-CT (QuantumFX, Perkin Elmer, Massachusetts, USA). In addition, a bone volume fraction (BV/TV, %) was measured. The measurement results of the bone mineral density of the femur are illustrated in FIG. 1, and the bone volume fraction is illustrated in FIG. 2.

As a result, as illustrated in FIG. 1, a significant increase in bone mineral density of the femur was observed in the group administered 1 mg/L of CHP compared to the ovariectomized group, and the result was similar to that of the positive control (risedronate). In addition, as illustrated in FIG. 2, the group administered 1 mg/L of CHP exhibited a bone volume fraction (BV/TV) restored to a level similar to that of the positive control (risedronate).

The significance of the experimental results was verified using a t-test by comparison among the ovariectomized group and the experimental groups treated with CHP, a zinc salt, a mixture of the CHP and the zinc salt, and risedronate, and the results showed statistically significant differences (*$p<0.05$).

Thus, it can be seen that the administration of 1 mg/L of CHP is effective in treating osteoporosis by increasing bone mineral density and the bone volume fraction.

Example 2

Evaluation of Efficacy of CHP on Promoting Osteogenic Differentiation of MC3T3-E1 and Bone Modeling 2-1. Culture Conditions of MC3T3-E1 Osteoblasts MC3T3-E1 cells were incubated in MEMα, an ascorbic acid-free medium containing 10% FBS and 1% penicillin/streptomycin, in a 5% $CO_2$ incubator at 37° C. To induce osteogenic differentiation, 10 mM β-glycerophosphate and 50 μg/μl of ascorbic acid was further added to the basal medium composition.

2-2. Induction of Osteogenic Differentiation of MC3T3-E1 According to Treatment with CHP or $hPTH_{1-34}$ as Positive Control 500 μl of 1×10$^5$ MC3T3-E1 cells were seeded into a 24-well plate and cultured for 24 hours until they reached 100% confluency. To induce osteogenic differentiation, the medium was replaced with a differentiation medium and as shown in Table 2, in a positive control, 10 nM $hPTH_{1-34}$ was treated, and the experimental groups were treated with 0.5 mM, 1 mM, or 2 mM CHP. At this time, in the undifferentiated group, which is a negative control for differentiation, a basal medium was used instead of the differentiation medium. In the positive control treated with $hPTH_{1-34}$, the medium was replaced with a differentiation medium 6 hours after the treatment. While the medium was replaced every 48 hours, each concentration of CHP and $hPTH_{1-34}$ was treated for a total of 14 days.

TABLE 2

| Group | 10 mM β-glycerophosphate 50 μg/μl ascorbic acid | 10 nM $hPTH_{1-34}$ (wash after 6 hours) | CHP |
|---|---|---|---|
| No differentiation | − | − | — |
| Negative Control | + | − | — |
| Positive control ($hPTH_{1-34}$) | + | + | — |
| Experimental group 1 (CHP 0.5 mM) | + | − | 0.5 mM |
| Experimental group 2 (CHP 1 mM) | + | − | 1 mM |
| Experimental group 3 (CHP 2 mM) | + | − | 2 mM |

2-3. Measurement of Alkaline Phosphatase (ALP) Activity

On day 14 of differentiation, the medium was removed, followed by washing once with PBS and fixing in 4% paraformaldehyde (PFA) at room temperature for 5 minutes. 500 μl of a 1-STEP™ NBCT/BCIP solution was added to allow a reaction to occur at room temperature for 1 hour. The reaction product was washed with distilled water, and then dried at room temperature, and the degree of coloring of the cells was observed using a microscope. Subsequently, DMSO was added to each well, followed by shaking, and then absorbance at 525 nm was measured.

As a result, as illustrated in FIG. 3, it was confirmed that the CHP-treated group showed a remarkably increased degree of coloring compared to the negative control and, as the concentration of CHP was increased, the increase in degree of coloring become larger. In particular, it was confirmed that the result of CHP 2 mM was a level similar to that of the positive control ($hPTH_{1-34}$ 10 nM) (see FIG. 4). From this, it can be construed that, as ALP activity is increased by CHP, CHP promotes osteogenic differentiation and bone modeling. Through this, it was determined that CHP is effective in bone health and osteoporosis treatment.

The invention claimed is:

1. A method for treating a bone loss disease in a subject in need thereof, consisting of administering an effective amount of a composition to the subject,
    wherein the composition consists of (i) cyclo-hispro or a pharmaceutically acceptable salt thereof, and (ii) a pharmaceutically acceptable carrier,
    wherein the composition does not contain zinc, and
    wherein the bone loss disease is caused by decreased osteogenic differentiation.

2. The method of claim 1, wherein the bone loss disease comprises any one or more selected from the group consisting of osteoporosis, Paget's disease, alveolar bone loss, osteomalacia, and renal osteodystrophy.

3. The method of claim 2, wherein the osteoporosis is caused by destruction of osteoblasts or reduced activity of osteoblasts.

4. A method for treating a bone loss disease in a subject in need thereof, consisting of administering to the subject an effective amount of a composition to the subject, wherein the composition consists of (i) a prostate extract comprising cyclo-hispro or a pharmaceutically acceptable salt thereof, and (ii) a pharmaceutically acceptable carrier; and wherein the bone loss disease is caused by decreased osteogenic differentiation.

5. The method of claim 4, wherein the prostate extract is in a form in which fat is removed.

6. The method of claim 4, wherein the bone loss disease comprises any one or more selected from the group consisting of osteoporosis, Paget's disease, alveolar bone loss, osteomalacia, and renal osteodystrophy.

7. The method of claim 6, wherein the osteoporosis is caused by decrease in female hormones, destruction of osteoblasts, or reduced activity thereof.

8. The method of claim 1, wherein the administering of the composition to the subject increases bone mineral density in the subject.

9. The method of claim 1, wherein the administering of the composition to the subject promotes osteogenic differentiation in the subject.

10. The method of claim 4, wherein the administering of the composition to the subject increases bone mineral density in the subject.

11. The method of claim 4, wherein the administering of the composition to the subject promotes osteogenic differentiation in the subject.

12. A method for enhancing bone mineral density in a subject in need thereof, comprising administering an effective amount of a composition to the subject,
wherein the composition comprises (i) cyclo-hispro or a pharmaceutically acceptable salt thereof, and (ii) a pharmaceutically acceptable carrier.

13. A method for promoting osteogenic differentiation in a subject in need thereof, comprising administering an effective amount of a composition to the subject,
wherein the composition comprises (i) cyclo-hispro or a pharmaceutically acceptable salt thereof, and (ii) a pharmaceutically acceptable carrier.

* * * * *